United States Patent
Drent et al.

(10) Patent No.: US 7,202,193 B2
(45) Date of Patent: Apr. 10, 2007

(54) PROCESS FOR THE CARBONYLATION OF AN ETHYLENICALLY UNSATURATED COMPOUND AND CATALYST THEREFORE

(75) Inventors: Eit Drent, Amsterdam (NL); Renata Helena Van Der Made, Amsterdam (NL); Robert Ian Pugh, Amsterdam (NL); Paul Gerard Pringle, Bristol (GB)

(73) Assignee: Shell Oil Company, Houston, TX (US)

( * ) Notice: Subject to any disclaimer, the term of this patent is extended or adjusted under 35 U.S.C. 154(b) by 349 days.

(21) Appl. No.: 10/505,019

(22) PCT Filed: Feb. 18, 2003

(86) PCT No.: PCT/EP03/01688

§ 371 (c)(1),
(2), (4) Date: Aug. 18, 2004

(87) PCT Pub. No.: WO03/070370

PCT Pub. Date: Aug. 28, 2003

(65) Prior Publication Data

US 2005/0090694 A1    Apr. 28, 2005

(30) Foreign Application Priority Data

Feb. 19, 2002   (EP) ................... 02251113

(51) Int. Cl.
*B01J 27/185* (2006.01)
*C07C 51/14* (2006.01)

(52) U.S. Cl. .................. 502/213; 560/522
(58) Field of Classification Search ................ None
See application file for complete search history.

(56) References Cited

U.S. PATENT DOCUMENTS

| 4,786,443 A | 11/1988 | Drent et al. ............. 260/549 |
| 6,156,934 A | 12/2000 | Suykerbuyk et al. ......... 568/12 |
| 2001/0051745 A1 | 12/2001 | Pearson et al. ............ 560/207 |
| 2003/0092935 A1* | 5/2003 | Ahlers ..................... 562/522 |
| 2005/0090694 A1 | 4/2005 | Drent et al. .............. 568/454 |

FOREIGN PATENT DOCUMENTS

| DE | 32511 | 10/1964 |
| DE | 1966944 | 6/1975 |
| DE | 10023470 | 11/2001 |
| DE | 10037961 | 2/2002 |
| WO | 98/42717 | 10/1998 |
| WO | 01/28972 | 4/2001 |
| WO | 01/72697 | 10/2001 |
| WO | 01/85662 | 11/2001 |

OTHER PUBLICATIONS

International Search Report dated Jun. 24, 2003.
Robert I. Pugh, et al, "Tandem isomerisation-carbonylation catalysis: highly active palladium(ii) catalysts for the selective methoxycarbonylation of internal alkenes to linear esters", Chemcomm Commun. 2001, pp. 1476-1477.
Ullman's Encyclopedia of Ind. Chem, 5th edition, 1986, vol. A5: "Cancer chemotherapy to ceramic colarants", pp. 222-223.
Robert Pugh, "Phospha-adamantanes a new class of bulky alkyl phosphine ligands", (thesis submitted to the University of Bristol, Apr. 2000) pp. 50-76.
Robert Pugh, et al., "Bis(phospha-adamantyl)alkanes: a new class of very bulky diphosphines", ChemComm, pp. 901-90226 Mar. 1999.
British Thesis by Joanne H. Downing, "Precious Metal Complexes of some novel functionalized secondary and tertiary phosphines", University of Bristol, Nov. 1992.
U.S. Appl. No. 10/504,913, filed Nov. 8, 2004, Drent et al.

* cited by examiner

*Primary Examiner*—Paul A. Zucker
(74) *Attorney, Agent, or Firm*—Donald F. Haas

(57) ABSTRACT

A process for the carbonylation of an ethylenically unsaturated compound with carbon monoxide and a co-reactant. The carbonylation reaction is carried out in the presence of a novel catalyst involving:
a) a source of a group VIII metal;
b) a bidentate diphosphine of formula I,

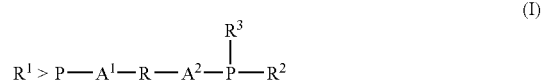

(I)

wherein $R^1$ represents a bivalent radical that together with the phosphorus atom to which it is attached is an optionally substituted 2-phospha-tricyclo[3.3.1.1{3,7}]- decyl group or a derivative thereof in which one or more of the carbon atoms are replaced by heteroatoms ("2-PA" group); wherein $R^2$ and $R^3$ independently represent univalent radicals of up to 20 atoms or jointly form a bivalent radical of up to 20 atoms; and wherein $A^1$ and $A^2$ independently represent optionally substituted alkylene groups and R represents an optionally substituted aromatic group; and,
c) a source of anions.

13 Claims, No Drawings

PROCESS FOR THE CARBONYLATION OF AN ETHYLENICALLY UNSATURATED COMPOUND AND CATALYST THEREFORE

FIELD OF THE INVENTION

The present invention relates to a process for the carbonylation of an ethylenically unsaturated compound with carbon monoxide and a co-reactant and a catalyst therefore. More specifically the present invention relates to a process for the preparation of a carboxylic acid, especially propanoic acid, or a derivative thereof by reaction of ethene with carbon monoxide and water or another appropriate co-reactant.

BACKGROUND OF THE INVENTION

WO-A-9842717 relates to the carbonylation of unsaturated compounds. In example 3 it describes the preparation of propanoic acid by reacting ethene with water in the presence of a catalyst comprising 0.1 mmol of palladium (II) acetate, 0.15 mmol of 1,3-PP'-di(2-phospha-1,3,5,7-tetramethyl-6,9,10-trioxatricyclo-[3.3.1.1{3.7}]decyl) propane and 0.2 mmol methyl sulphonic acid. Ethene was fully converted with 100% selectivity into propanoic acid at an average rate of 1500 mol/mol.hr.

WO-A-0172697 relates to the carbonylation of pentenenitrile to prepare cyanovaleric acid in the presence of a catalyst comprising a specific bidentate phosphine, arsine or stibine ligand. In this bidentate ligand the P, As or Sb atoms are connected via an organic bridging group and each substituted with two tertiary alkyl groups.

In the description a broad variety of possible bridging groups are mentioned. Although, in passing, divalent aryl groups, viz. dixylyl, are mentioned, preference is given to $C_3$–$C_5$ alkylene groups.

Furthermore a broad variety of possible tertiary alkyl groups are mentioned. In passing, it is mentioned that the tertiary alkyl groups include cyclic structures, viz. an alkyl substituted 2-phosphatricyclo [3.3.1.1{3,7}]decyl group. Preference, however, is given to bidentate diphosphines containing non-cyclic tertiary alkyl groups, such as tert.-butyl groups. These preferences are confirmed in the examples. The use of a catalyst comprising 1,3-bis (di-tert.-butylphosphino) propane as a ligand, viz. example 3 and 8, results in a higher reaction rate and conversion than the use of a catalyst comprising 1,2-bis (di-tert.-butylphosphinomethyl) benzene as a ligand, viz. example 9. Furthermore the use of a catalyst comprising 1,3-bis (di-tert-butylphosphino) propane as a ligand, viz. example 1, results in a higher reaction rate and conversion than the use of a catalyst comprising 1,3-PP'-di(2-phospha-1,3,5,7-tetramethyl-6,9,10-trioxatricyclo-[3.3.1.1{3.7}]decyl) propane as a ligand, viz. example 10.

WO-A-0185662 relates to a process for producing aldehydes by hydroformylation of a vinyl-group containing compound. The object of the invention was to obtain a high selectivity towards the normal product. The hydroformylation reaction is carried out in the presence of a catalyst comprising a group VIII metal and a diphosphine ligand containing two 2-phospha-tricyclo[3.3.1.1{3.7}]-decyl groups connected by a bridge X. A wide range of possible bridges are indicated by their generic formulae. However, only diphosphine ligands having a "ethane", "propane" and "hexane" bridge are specifically mentioned. The examples disclose only the use of a catalyst containing rhodium dicarbonyl acetylacetonate and 1,3-PP'-di(2-phospha-1,3,5,7-tetramethyl-6,9,10-trioxatricyclo[3.3.1.1{3.7}]decyl) propane.

In section 3.2 of his thesis "Phospha-adamantanes a new class of bulky alkyl phosphine ligands" (thesis submitted to the University of Bristol in April 2000), Robert Pugh describes the synthesis of 1,2-P,P'-di(2-phospha-1,3,5,7-tetramethyl-6,9,10-trioxatricyclo[3.3.1.1{3.7}decyl)-o-xylene. No applications are indicated for this ligand.

Although the processes as described in WO-A-9842717 and WO-A-0172697 result in more than satisfactory reaction rates, there is still room for improvement. A process resulting in even higher reaction rates is therefore desirable.

SUMMARY OF THE INVENTION

Accordingly the present invention provides a process for the carbonylation of an ethylenically unsaturated compound with carbon monoxide and a co-reactant in the presence of a catalyst comprising:
a) a source of a group VIII metal;
b) a bidentate diphosphine of formula I,

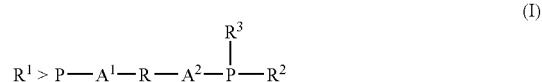

wherein $R^1$ represents a bivalent radical that together with the phosphorus atom to which it is attached is an optionally substituted 2-phospha-tricyclo[3.3.1.1{3,7}]-decyl group or a derivative thereof in which one or more of the carbon atoms are replaced by heteroatoms ("2-PA" group); wherein $R^2$ and $R^3$ independently represent univalent radicals of up to 20 atoms or jointly form a bivalent radical of up to 20 atoms; and wherein $A^1$ and $A^2$ independently represent optionally substituted alkylene groups and R represents an optionally substituted aromatic group; and
c) a source of anions.

The processes of the present invention results in high reaction rates.

DETAILED DESCRIPTION OF THE INVENTION

In the process according to the invention the ethylenically unsaturated compound is preferably an alkene having from 2 to 20, more preferably from 2 to 10, and most preferably from 2 to 4 carbon atoms. The alkene can be normal, branched or can comprise a cyclic structure. The alkene can comprise one or more double bonds per molecule and those double bonds can be internal or terminal. In the alkene one or more hydrogen atoms may have been replaced by other atoms, such as halogen atoms, sulphur atoms, oxygen atoms or nitrogen atoms, or by groups of atoms, such as hydroxyl groups; cyano groups; alkoxy groups, such as methoxy or ethoxy groups; thioxy groups; amino groups such as dimethyl- and diethyl-amino groups; or aromatic groups, such as phenyl, tolyl or naphthyl groups. Preferably the alkene contains no heteroatoms.

Examples of alkenes include ethene, propene, 1- or 2-butene, 1- or internal pentene, 1- or internal hexene, 1- or internal heptene, 1- or internal octene, 1- or internal decene, internal or terminal $C_{14}$–$C_{18}$ olefins, pentenenitrils, cyclohexene and styrene. Preferred alkenes include ethene, propene, 1-butene and 2-butene. Ethene is especially preferred.

In the process according to the present invention, the carbon monoxide can be used in its pure form or diluted with an inert gas such as nitrogen, carbon dioxide or noble gases such as argon. If the ethylenically unsaturated compound is a gas, e.g. ethene, a gaseous mixture of carbon monoxide and the ethylenically unsaturated compound can be used. If the co-reactant is hydrogen, a gaseous mixture of carbon monoxide and hydrogen can be used.

The process according to the invention can be carried out with a wide range of co-reactants, including for example molecular hydrogen, water, monohydric alkanols, such as methanol, ethanol, isopropanol and 1-butanol, and polyhydric alkanols, such as ethylene glycol, 1,4-butanediol and glycerol; thiols; aromatic alkanols such as phenol; primary or secondary (poly-) amines or amides, such as diethylamine, N,N-dimethyl ethylenediamine; and carboxylic acids, for example acetic acid, pivalic acid and propanoic acid.

Of these, molecular hydrogen and hydroxyl group containing compounds, such as water, alkanols and carboxylic acids are preferred. Of these, the hydroxyl-group containing compounds are especially preferred for the preparation of carboxylic acids and their derivatives. Preferred hydroxyl group containing compounds include water, monohydric alkanols having from 1 to 6 carbon atoms per molecule, such as methanol, ethanol, propanol and 1-butanol, dihydric alkanols having from 2 to 6 carbon atoms, such as ethylene glycol and 1,4-butanediol and phenol. Most preferably the co-reactant is water.

The process is carried out in the presence of a specific novel catalyst. The present invention therefore also relates to a catalyst comprising:
a) a source of a group VIII metal;
b) a bidentate diphosphine of formula I,

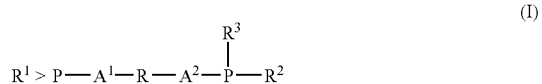

(I)

wherein $R^1$ represents a bivalent radical that together with the phosphorus atom to which it is attached is an optionally substituted 2-phospha-tricyclo[3.3.1.1{3,7}]-decyl group or a derivative thereof in which one or more of the carbon atoms are replaced by heteroatoms ("2-PA"-group); wherein $R^2$ and $R^3$ independently represent univalent radicals of up to 20 atoms or jointly form a bivalent radical of up to 20 atoms; and wherein $A^1$ and $A^2$ independently represent optionally substituted alkylene groups and R represents an optionally substituted aromatic group; and
c) a source of anions.

Examples of group VIII metals that can be used include Ru, Rh, Ni, Pd and Pt. Preferably a source of group 10 metal is used, such as Ni, Pd or Pt, or group 9 metal Rhodium. Of these, palladium and platinum are more preferred. Palladium is especially preferred.

Examples of suitable metal sources are platinum or palladium compounds such as salts of palladium or platinum and carboxylic acids with up to 12 carbon atoms, palladium- or platinum complexes, e.g. with carbon monoxide or acetylacetonate, or palladium or platinum combined with a solid material such as an ion exchanger. Palladium (II) acetate, palladium dibenzylacetone and platinum (II) acetylacetonate are examples of preferred metal sources.

In the diphosphine of formula I, R represents an optionally substituted aromatic group which is linked to the phosphorus atoms via the alkylene groups. The aromatic group can be a monocyclic group, such as for example a phenyl group; or a polycyclic group, such as for example naphthyl, anthryl or indyl group. Preferably, the aromatic group R contains only carbon atoms, but R can also represent an aromatic group wherein a carbon chain is interrupted by one or more hetero atoms, such as nitrogen, sulphur or oxygen atom in for example a pyridine, pyrrole, furan, thiophene, oxazole or thiazole group. Most preferably the aromatic group R represents a phenyl group.

Optionally the aromatic group is substituted. Suitable substituents include groups containing hetero-atoms such as halides, sulphur, phosphorus, oxygen and nitrogen. Examples of such groups include chloride, bromide, iodide and groups of the general formula —O—H, —O—$X^2$, —CO—$X^2$, —CO—O—$X^2$, —S—H, —S—$X^2$, —CO—S—$X^2$, —$NH_2$, —$NHX^2$, —$NR^2X^3$, —$NO_2$, —CN, —CO—$NH_2$, —CO—$NHX^2$, —CO—$NX^2X^3$ and —$Cl_3$, in which $X^2$ and $X^3$, independently, represent alkyl groups having from 1 to 4 carbon atoms like methyl, ethyl, propyl, isopropyl and n-butyl.

If the aromatic group is substituted it is preferably substituted with one or more aryl, alkyl or cycloalkyl groups, preferably having from 1 to 10 carbon atoms. Suitable groups include, methyl, ethyl, propyl, iso-propyl, butyl and iso-butyl, phenyl and cyclohexyl. Most preferably, however, the aromatic group is non-substituted and only linked to the alkylene groups which connect it with the phosphorus atoms. Preferably the alkylene groups are connected at adjacent positions, for example the 1 and 2 positions, of the aromatic group.

Preferably the alkylene groups $A^1$ and $A^2$ are each independently a lower alkylene group. By a lower alkylene group is understood an alkylene group comprising from 1 to 4 carbon atoms. Each alkylene groups can independently be substituted, for example with alkyl groups, or non-substituted. Preferably the alkylene groups are both non-substituted. More preferably the alkylene groups are both unsubstituted methylene or ethylene groups, most preferably methylene groups.

$R^1$ in the diphosphine of formula I represents a bivalent radical that together with the phosphorus atom to which it is attached is an optionally substituted 2-phospha-tricyclo [3.3.1.1{3,7}]decyl group or a derivative thereof in which one or more of the carbon atoms are replaced by heteroatoms.

Tricyclo[3.3.1.1{3,7}]decane is the systematic name for a compound more generally known as adamantane. Therefore, the optionally substituted 2-phospha-tricyclo-[3.3.1.1{3,7}decyl group or a derivative thereof will be referred to as "2-PA" group (as in 2-phosphadamantyl group) throughout the specification.

Preferably, the 2-PA group is substituted on one or more of the 1, 3, 5 or 7 positions with a monovalent radical $R^5$ of up to 20 atoms, preferably of 1 to 10 carbon atoms and more preferably of 1 to 6 carbon atoms. Examples of $R^5$ include methyl, ethyl, propyl, phenyl, and 4-dodecylphenyl. More preferably, the 2-PA group is substituted on each of the 1, 3, 5 and 7 positions, suitably with identical radicals $R^5$.

The 2-PA group has preferably additional heteroatoms other than the 2-phosphorus atom in its skeleton. Suitable heteroatoms are oxygen and sulphur atoms. Suitably, these heteroatoms are found in the 6, 9 and 10 positions.

The most preferred bivalent radical is the 2-phospha-1,3, 5,7-tetramethyl-6,9,10-trioxadamantyl group.

If $R^2$ and $R^3$ each independently represent univalent radicals of up to 20 atoms, they preferably represent univalent radicals of in the range from 1 to 10 carbon atoms. The univalent radicals can be aliphatic, aromatic or cycloaliphatic, and can be straight or branched. The radicals can each independently comprise heteroatoms such as N, O and S, but preferably comprise only carbon atoms. Examples of univalent radicals include hydrocarbyl groups such as, for instance, methyl, ethyl, propyl, tert.-butyl, cyclohexyl, phenyl, pyridyl, and (substituted) trimethylsilyl or alkoxy groups. Alternatively, $R^2$ and $R^3$ may together form a bivalent radical, such as 1,6-hexylene, 1,3 or 1,4-cyclooctylene. Preferably, $R^2$ and $R^3$ together with the phosphorus atom form a 2-PA group as described herein before. Most preferably $R^2$ and $R^3$ together with the phosphorus atom form a 2-PA group identical to $R^1$.

An especially preferred bidentate diphosphine is a diphosphine wherein $R^2$ and $R^3$ together with the phosphorus atom form a 2-PA group similar, and more preferably identical, to $R^1$, wherein the 2-PA groups are preferably connected by a ortho-xylyl group. Preferences for the 2-PA groups are indicated herein above.

Most preferably the diphosphine is a compound according to Formula II, wherein $R^5$ represents alkyl groups of 1 to 6 carbon atoms, preferably methyl.

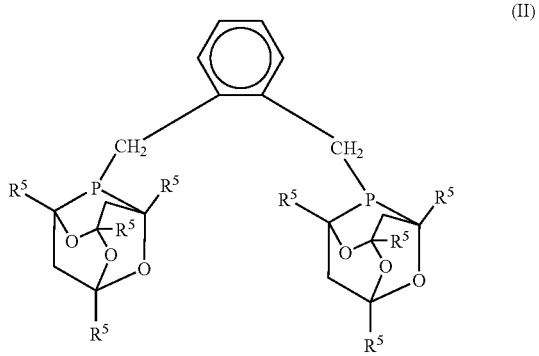

(II)

A very advantageous bidentate diphosphine in the process of the present invention is 1,2-P,P'-di(2-phospha-1,3,5,7-tetramethyl-6,9,10-trioxatricyclo-[3.3.1.1{3.7}]decyl)-methylene-benzene (also sometimes referred to as 1,2-P,P'-di(2-phospha-1,3,5,7-tetramethyl-6,9,10-trioxatricyclo [3.3.1.1{3.7}]decyl)-ortho-xylene).

The bidentate ligands used in the process according to the invention can be prepared as described for example by Robert Pugh in his theses "Phospha-adamantanes a new class of bulky alkyl phosphine ligands" (thesis submitted to the University of Bristol in April 2000).

Preferably, however, the bidentate ligands are prepared by a process wherein the phosphorus groups are introduced via a 2-phospha-tricyclo[3.3.1.1{3,7}]decane group or a derivative thereof, instead of via an arylalkyl group having two primary phosphorus groups.

The preferred process for preparing the bidentate ligands comprises three synthetic steps.

In a first synthetic step an appropriate 2-phosphatricyclo [3.3.1.1{3,7}]decane group or a derivative thereof is reacted with the hydride of a group 13 metal, including for example B, Al and Ga. Of these $BH_3$ is preferred. The first step reaction can be carried out at a wide range of temperatures. Suitably the temperature lies within a range from –150° C. to 100° C. Preferably the reaction is carried out at temperatures in the range for –50 to 50° C. and more preferably from –10 to 10° C. Preferably the reaction is carried out in a solvent as stipulated below. The formed adduct is preferably recrystallised before use in the subsequent second step.

In a second subsequent synthetic step the group 13 adduct of the 2-phospha-tricyclo[3.3.1.1{3,7}]decane group or a derivative thereof is reacted in a first sub-step with an alkylated group I A metal, preferably Na or Li, most preferably a lithium alkyl. The reaction can be carried out at a temperature in the range from –150° C. to 100° C., preferably carried out at a temperature in the range from –100° C. to 0° C., and more preferably a temperature from –80 to –50° C. The in-situ prepared lithium phosphide is subsequently reacted in a second sub-step with an appropriate halogenated arylalkyl group of the formula

H-A¹-R-A²-H (III)

wherein H represents F, Cl, Br, I, and preferably Cl or Br; and $A^1$, $A^2$ and R represent groups as defined herein before.

The reaction can be carried out at a temperature in the range from –150° C. to 100° C. The reaction is preferably carried out at a temperature below 0° C., preferably a temperature from –80 to –50° C. Preferably the reactions of the second synthetic step are carried out in a solvent as stipulated below.

In a third synthetic step the group 13 protecting group is removed from the bidentate diphosphine group 13 adduct. The removal of the group 13 protecting group can conveniently be achieved directly after the second synthetic step by refluxing with an amine. Amines that can be used include mono- or polyamines. Suitable examples include dialkyl and trialkylamines wherein the alkyl groups preferably have in the range from 1 to 6 carbon atoms, such as diethylamine, triethylamine, dimethylamine and trimethylamine; triarylamines such as triphenylamine; arylalkylamines such as diethylphenylamine and dimethylphenylamine; and cyclic structures containing nitrogen atoms such as 1,4-diazabicyclo[2,2,2]octane. Of these dimethylamine and diethylamine are preferred. Diethylamine is especially preferred. The second and third synthetic step are preferably carried without an intermediate recrystallisation step. The reaction product of the third synthetic step is subsequently preferably recrystallised before use as a bidentate diphosphine ligand.

All reaction steps are preferably carried out in a solvent. Examples of suitable solvents include saturated hydrocarbons such as, e.g., paraffins and isoalkanes; ethers such as 2,5,8-trioxanonane (diglyme), diethylether, tetrahydrofuran and anisole; sulphones such as sulpholane, and aromatic hydrocarbons such as toluene. In the first synthetic step halogenated saturated alkanes such as dichloromethane might also be used as a solvent. A preferred solvent for all synthetic steps is tetrahydrofuran.

As a source of anions, any compound generating these anions may be used. Suitably, acids, or salts thereof, are used as source of anions, for example any of the acids mentioned above, which may also participate in the salts of the group VIII metal.

Preferably acids are used as anion source having a pKa value of less than 6, more preferably less than 5, measured in aqueous solution at 18° C. Examples of suitable anions are anions of carboxylic acids; phosphoric acid; sulphuric acid; sulphonic acids, such as methanesulphonic acid, trifluoromethanesulphoni-c acid, tert-butane-sulphonic acid, p-toluenesulphonic acid and 2,4,6-trimethylbenzene-sulphonic acid; and halogenated carboxylic acids such as trifluoroacetic acid.

Also, complex anions are suitable, such as the anions generated by a combination of a Lewis acid such as $BF_3$, AlCl$_3$, SnF$_2$, Sn(CF$_3$SO$_3$)$_2$, SnCl$_2$ or GeCl$_2$, with a protic acid, such as a sulphonic acid, e.g. CF$_3$SO$_3$H or CH$_3$SO$_3$H or a hydrohalogenic acid such as HF of HCl, or a combination of a Lewis acid with an alcohol. Examples of such complex anions are BF$_4$—, SnCl$_3$—, [SnCl$_2$.CF$_3$SO$_3$]— and PF$_6$—.

Preferably the source of anions is a carboxylic acid. More preferably a carboxylic acid having a pKa of below 6, more preferably a carboxylic acid with a pKa in the range from 2 to 6 and most preferably a carboxylic acid with a pKa in the range from 4 to 6, measured in aqueous solution at 18° C. Preferred carboxylic acids that can be used include carboxylic acids with up to 15 carbon atoms, preferably with up to 10 carbon atoms. Such carboxylic acids can be branched, linear or cyclic and can be saturated or non-saturated. Examples of suitable carboxylic acids include pentanoic acid, pivalic acid, propanoic acid and propenoic acid.

When the process according to the invention is used to prepare a carboxylic acid, this carboxylic acid is a preferred source of anions, such that the anions complexing with the group VIII metal are anions of the carboxylic acid. For example, the carbonylation of ethene with carbon monoxide and water to prepare propanoic acid is advantageously carried out using propanoic acid as a source of anions. Preferably essentially no anions of any additional acids "stronger" than the carboxylic acid, i.e. acids having a pKa higher than that of the carboxylic acid in the used solvent, are present.

In the process of the invention, the starting materials and the formed carbonylation product can act as reaction diluent, but also an additional (inert) solvent can be present. Examples of additional solvents include saturated hydrocarbons such as, e.g., paraffins and isoalkanes are recommended and furthermore ethers such as 2,5,8-trioxanonane (diglyme), diethylether and anisole; sulphones such as sulpholane, and aromatic hydrocarbons such as toluene.

In a preferred embodiment a carboxylic acid is used as a reaction diluent. Preferably a carboxylic acid having a pKa of below 6, more preferably a carboxylic acid with a pKa in the range from 2 to 6 and most preferably a carboxylic acid with a pKa in the range from 4 to 6, measured in aqueous solution at 18° C. When the process according to the invention is used to prepare a carboxylic acid, this carboxylic acid is a preferred reaction diluent. For example, the carbonylation of ethene with carbon monoxide and water to prepare propanoic acid is advantageously carried out in propanoic acid as a solvent.

Carbon monoxide partial pressures in the range of 1–65 bar are preferred. The carbonylation reaction is conveniently carried out at moderate temperatures. Accordingly, the process is suitably carried out at a temperature in the range of. 30 to 200° C., preferred temperatures being in the range of 50 to 150° C. The reaction pressures may also vary widely. For instance, the reaction can be carried out with pressures in the range of 1 to 100 bar, pressures in the range of 2 to 30 bar being preferred.

The ethylenically unsaturated compound and co-reactant are suitably supplied in a molar ratio within the range of 10:1 to 1:10, preferably within the range of 5:1 to 1:5, more preferably within the range of 2:1 to 1:2.

The quantity, in which the catalyst is used, is not critical and may vary within wide limits. For practical reasons amounts in the range of $10^{-8}$ to $10^{-1}$, preferably in the range of $10^{-7}$ to $10^{-2}$ mole atom of group VIII metal per mole of unsaturated compound can be used.

For the preparation of the catalysts of the invention, the amount of bidentate diphosphine ligand can be applied in some excess of the amount of the group VIII metal, expressed as moles of ligand per mole atom of the group VIII metal.

Preferably the amount of ligand is selected such that per mole atom of the group VIII metal 0.5 to 10 moles of ligand are present. More preferably the molar amount of bidentate diphoshine ligand per mole of group VIII metal is in the range of 1 to 3, and most preferably in the range of 1 to 2. In the presence of oxygen, slightly higher amounts can be beneficial.

The amount of the anion source may vary widely depending on whether the carboxylic acid is simultaneously the reaction product or the co-reactant or simultaneously used as a solvent. For practical reasons the amount of source of anions is at least 0.5 moles per mole of group VIII metal. Preferably the amount of source of anions varies in a range from 0.5 to $10^7$, preferably from 1 to $10^6$ moles per mole of group VIII metal.

The process according to the invention can be carried out batch-wise, semi-continuously and continuously. If the process is carried out semi-continuously, appropriate additional amounts of carbon monoxide and/or ethylenically unsaturated compound and/or co-reactant are preferably added intermittently at appropriate stages in the process. Preferably the process is carried out continuously.

The carbonylation product prepared in the process according to the invention can be used in a wide range of applications. In an especially preferred embodiment the process according to the invention is used to prepare a carboxylic acid by carbonylation of an ethylenically unsaturated compound with carbon monoxide and water. The prepared carboxylic acid can, in turn be used for the preparation of a carboxylic anhydride by carbonylation of an ethylenically unsaturated compound with carbon monoxide using the carboxylic acid as a co-reactant.

The invention therefore also provides a process for the preparation of a carboxylic acid and its corresponding carboxylic anhydride comprising:

A) carbonylation of an ethylenically unsaturated compound with carbon monoxide and water in the presence of a catalyst according to the process as described herein, to yield an carboxylic acid;

B) carbonylation of an ethylenically unsaturated compound with carbon monoxide and the carboxylic acid obtained in step A) in the presence of a catalyst, to yield an carboxylic anhydride.

The catalyst in step B) is preferably a catalyst comprising:
i) a source of group VIII metal;
ii) a phosphorus containing ligand; and
iii) a source of anions.

The source of group VIII metal i) is preferably a source of group VIII metal as described hereinbefore.

The phosphorus containing ligand ii) is preferably a bidentate diphoshine. Preferred bidentate diphosphines include those described in WO-A-9842717 and WO-A-0172697 are hereby incorporated by reference, and those bidentate diphosphines described hereinbefore. Especially preferred bidentate diphosphines include 1,3-P,P'-di(2-phospha-1,3,5,7-tetramethyl-6,9,10-trioxatricyclo[3.3.1.1{3.7}] decyl)propane and 1,2-P,P'-di(2-phospha-1,3,5,7-tetraxnethyl-6,9,10-trioxatricyclo-[3.3.1.1{3.7}]decyl)-methylene-benzene (also sometimes referred to as 1,2-P,P'-di(2-phospha-1,3,5,7-tetramethyl-6,9,10-trioxatricyclo-[3.3.1.1{3.7}]decyl)-ortho-xylene).

The source of anions iii) is preferably a source of anions as described herein before. The carboxylic acid as prepared in step A) is especially preferred as a source of anions. In a preferred embodiment essentially no anions of any additional acids "stronger" than the carboxylic acid, i.e. acids having a pKa higher than that of the catboxylic acid in the used solvent, are present.

The ethylenically unsaturated compound in step A) or in step B) can independently be any of the ethylenically unsaturated compounds mentioned herein before. The ethylenically unsaturated compound in step A) and step B) can be the same or different.

If the ethylenically unsaturated compound in step A) and B) are the same, a symmetrical carboxylic anhydride is advantageously obtained in step B).

In an especially preferred embodiment the ethylenically unsaturated compound in step A) and in step B) is ethene. In this case propanoic acid and propanoic anhydride are obtained at high reaction rates and in good selectivity.

The ethylenically unsaturated compound in step A) and B) can also be chosen such that a specific asymmetrical carboxylic anhydride is obtained in step B).

Reaction conditions for step B), e.g. temperature and pressure, are preferably as described herein before for step A).

The process steps A) and B) can be carried out in a wide range of solvents, including the ones mentioned herein before. Preferably steps A) and B) are carried out in the same solvent and most preferably the solvent in both step A) and step B) is the carboxylic acid as prepared in step A).

The present invention advantageously allows steps A) and B) to be carried out simultaneously, for example in one reactor. In such a process carboxylic anhydride can advantageously be prepared at high rate and with good selectivity using as starting compounds an ethylenically unsaturated compound, carbon monoxide and water.

An carboxylic anhydride prepared by this process can be used for various applications. In a preferred application the carboxylic anhydride is used as an acylation agent. The carboxylic anhydride can for example be used in the acylation of aromatic alcohols such as for example phenol to prepare the corresponding carboxylic ester. Another example is the acylation of amines or amides to respectively amides or imides. By acylation of diamines such as ethylene diamine and propylene diamine, bleach activators such as respectively tetra acetyl ethylene diamine and tetra acetyl propylene diamine can be prepared.

The prepared carboxylic anhydride can also react with acetic acid in a equilibrium reaction to prepare acetic anhydride, a compound which is otherwise difficult to obtain.

The invention will now be illustrated by the following non-limiting examples.

COMPARATIVE EXAMPLE A

An autoclave was charged 50 ml propionic acid, 5 ml water, 0.1 mmol Pd(OAc)$_2$ and 0.15 mmol 1,3-PP'-di(2-phospha-1,3,5,7-tetramethyl-6,9,10-trioxatricyclo-[3.3.1.1{3.7}]decyl) propane. After being flushed, the autoclave was next pressurized with a partial pressure of 15 bar carbon monoxide and 10 bar ethene. Following sealing of the autoclave, its contents were heated to a temperature of 100° C. and maintained at that temperature for 1.5 hours. After cooling, a sample was taken from the contents of the autoclave and analysed by Gas Liquid Chromatography. The average rate of the reaction, expressed as mol product per mol Pd per hour, was also calculated. The average rate of reaction is defined as the mean rate of carbon monoxide consumption during a period up to exhaustion of either one of ethene or carbon monoxide.

Ethene was fully converted with 100% selectivity into propionic acid at an average rate of 2500 mol per mol Pd per hour (mol/mol.hr). The average rate of reaction was defined as the mean rate of carbon monoxide consumption during a period up to the exhaustion of either one of ethene or carbon monoxide.

EXAMPLE 1

Comparative example A was repeated, however using 0.15 mmol 1,2-P,P'-di(2-phospha-1,3,5,7-tetramethyl-6,9,10-trioxatricyclo[3.3.1.1{3.7}]decyl)-methylene-benzene instead of 0.15 mmol 1,3-PP'-di(2-phospha-1,3,5,7-tetramethyl-6,9,10-trioxatricyclo[3.3.1.1{3.7}]-decyl) propane and using 10 bar instead of 15 bar carbon monoxide. The autoclave was cooled after 1 hour.

Ethene was fully converted with 100% selectivity into propionic acid at an average rate of 10000 mol/mol.hr.

COMPARATIVE EXAMPLE B

Example 1 was repeated, however using 0.15 mmol 1,2-bis(di-t-butylphosphino)-methylene-benzene, instead of 0.15 mmol 1,2-P,P'-di(2-phospha-1,3,5,7-tetramethyl-6,9,10-trioxatricyclo[3.3.1.1{3.7}decyl)-o-xylene. The autoclave was cooled after 5 hours.

Ethene was converted with 100% selectivity into propionic acid at an average rate of 800 mol/mol.hr.

EXAMPLE 2

Semi-continuous

Example 1 was repeated, however-using 32 ml instead of 5 ml water and 20 bar of an 1:1 gas mixture of ethene and carbon monoxide. The gas mixture was introduced to the autoclave 30 times in portions of 5–15 bar over 2 hours at a process temperature of 100° C.

Ethene/CO were fully converted with 100% selectivity into propionic acid at an average rate of 10000 mol/mol.hr.

EXAMPLE 3

An autoclave was charged with 15 ml methyl-3-pentenoate and 40 ml toluene as a solvent, 0.1 mmol rhodium dicarbonyl acetylacetonate and 0.15 mmol 1,2-PP'-di(2-phospha-1,3,5,7-tetramethyl-6,9,10-trioxatricyclo [3.3.1.1{3.7}]decyl)-methylene-benzene. After being flushed, the autoclave was next pressurized with a partial pressure of 30 bar carbon monoxide and 30 bar hydrogen. Following sealing of the autoclave, its contents were heated to a temperature of 100° C. and maintained at that temperature for 1 hour. After cooling, a sample was taken from the contents of the autoclave and analysed by Gas Liquid Chromatography. Conversion of methyl-3 pentenoate was 100%. The selectivity towards 2-formyl methyl pentanoate was 3,5%, 3-formyl methyl pentanoate 51.3%, 4 formyl methyl pentanoate 39.4% and 5 formyl pentanoate 4.0%. The average rate of conversion towards these products was 2500 mol per mol Rh per hour (mol/mol.hr).

EXAMPLE 4

Synthesis of 1,2-P,P'-di(2-phospha-1,3,5,7-tetramethyl-6,9,10-trioxatricyclo[3.3.1.1{3.7}decyl)-methylene-benzene Synthesis Step 1:

To a solution of 2-phospha-1,3,5,7-tetramethyl-6,9,10-trioxatricyclo[3.3.1.1{3.7}]decane hydride (H-PA) (13 g, 60 mmol) in tetrahydrofuran (40 ml) was added a 1 M solution of Boron trihydride (73 mmol) in tetrahydrofuran over 5 min at 0° C. After 4 h stirring at room temperature (20° C.), the solvent was removed and the crude product was recrystallised from the minimum volume hot tetrahydrofuran (20 ml) and washed with hexane (2×5 ml) to afford 2-phospha-1,3,5,7-tetramethyl-6,9,10-trioxatricyclo[3.3.1.1{3.7}]decane borane (H-PA.BH$_3$) as colourless crystals. Further product was obtained by recrystallisation of the filtrate from hot tetrahydrofuran (7 ml). The yield of H-PA.BH$_3$ was 86% based on H-PA.

Synthesis Step 2:

To a solution of H-PA.BH$_3$ (3.67 g. 16 mmol) in tetrahydrofuran (40 ml) was added hexyllithium (6.4 ml (2.5 M), 16 mmol) at −75° C. After stirring for 1 h, α,α'-dibromo-o-xylene (2.1 g, 8 mmol) in tetrahydrofuran (20 ml) was added at −75° C. and the reaction allowed to warm to room temperature. After 3 hours, diethylamine (3 ml, 28 mmol) was added and the reaction refluxed for 2 hours. After cooling, the solvent was removed and the crude product dissolved in toluene (60 ml) and washed with water (4×40 ml). The solvent was removed to afford 1,2-P,P'-di(2-phospha-1,3,5,7-tetraniethyl-6,9,10-trioxatricyclo-[3.3.1.1{3.7}] decyl)-methylene-benzene (3.9 g, 91%) as a white solid (see thesis by Robert Pugh submitted to the University of Bristol in April 2000 for NMR characterization) is hereby incorporated by reference. The diphosphine may be further purified by recrystallization from methanol.

What is claimed is:

1. A process for the carbonylation of an ethylenically unsaturated compound with carbon monoxide and a co-reactant in the presence of a catalyst comprising:
    a) a source of a group VIII metal;
    b) a bidentate diphosphine of formula I,

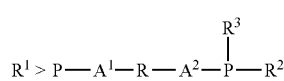

(I)

wherein R$^1$ represents a bivalent radical that together with the phosphorus atom to which it is attached is an optionally substituted 2-phospha-tricyclo[3.3.1.1{3,7}]-decyl group or a derivative thereof in which one or more of the carbon atoms are replaced by heteroatoms ("2-PA" group); wherein R$^2$ and R$^3$ independently represent univalent radicals of up to 20 atoms or jointly form a bivalent radical of up to 20 atoms; and wherein A$^1$ and A$^2$ independently represent optionally substituted alkylene groups and R represents an optionally substituted aromatic group; and,
    c) a source of anions.

2. A catalyst comprising:
    a) a source of palladium or rhodium;
    b) a bidentate diphosphine of formula I,

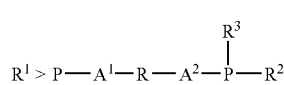

(I)

wherein R$^1$ represents a bivalent radical that together with the phosphorus atom to which it is attached is an optionally substituted 2-phospha-tricyclo[3.3.1.1{3,7}]-decyl group or a derivative thereof in which one or more of the carbon atoms are replaced by heteroatoms ("2-PA" group); wherein R$^2$ and R$^3$ independently represent univalent radicals of up to 20 atoms or jointly form a bivalent radical of up to 20 atoms; and wherein A$^1$ and A$^2$ independently represent optionally substituted alkylene groups and R represents an optionally substituted aromatic group; and,
    c) a source of anions.

3. The catalyst of claim 2 wherein R$^2$ and R$^3$ together with the phosphorus atom form a 2-PA group identical to R$^1$.

4. The catalyst of claim 3 wherein the bidentate diphosphine is 1,2-P,P'-[di-(2-phospha-1,3,5,7-tetramethyl-6,9,10-trioxatricyclo[3.3.1.1{3.7}decyl)-methylene]-benzene.

5. The catalyst of claim 2 wherein the source of anions is a carboxylic acid.

6. The process of claim 1 wherein the catalyst is a catalyst comprising:
    a) a source of palladium or rhodium;
    b) a bidentate diphosphine of formula I,

(I)

wherein R$^1$ represents a bivalent radical that together with the phosphorus atom to which it is attached is an optionally substituted 2-phospha-tricyclo[3.3.1.1{3,7}]-decyl group or a derivative thereof in which one or more of the carbon atoms are replaced by heteroatoms ("2-PA" group); wherein R$^2$ and R$^3$ independently represent univalent radicals of up to 20 atoms or jointly form a bivalent radical of up to 20 atoms; and wherein A$^1$ and A$^2$ independently represent optionally substituted alkylene groups and R represents an optionally substituted aromatic group; and,
    c) a source of anions.

7. The process of claim 1 wherein a carboxylic acid is used as a reaction diluent.

8. A process for the preparation of a carboxylic acid and its corresponding carboxylic anhydride comprising the following steps:
    a) carbonylation of an ethylenically unsaturated compound with carbon monoxide and water to yield a carboxylic acid, said carbonylation being carried out in the presence of a catalyst comprising:
        i) a source of a group VIII metal;
        ii) a bidentate diphosphine of formula I,

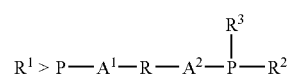

(I)

wherein R1 represents a bivalent radical that together with the phosphorus atom to which it is attached is an optionally substituted 2-phospha-tricyclo[3.3.1.1{3,7}]-decyl group or a derivative thereof in which one or more of the carbon atoms are replaced by heteroatoms ("2-PA" group); wherein R2 and R3 independently represent univalent radicals of up to 20 atoms or jointly form a bivalent radical of up to 20 atoms; and wherein A1 and A2 independently represent optionally substituted alkylene groups and R represents an optionally substituted aromatic group; and,
        iii) a source of anions; and b) carbonylation of an ethylenically unsaturated compound with carbon monoxide and the carboxylica acid obtained in step a) in the presence of a catalyst to yield a carboxylic anhydride.

9. The process of claim 8 wherein the catalyst in step b) is a catalyst comprising:
  i) a source of group VIII metal;
  ii) a phosphorus containing ligand; and
  iii) a source of anions.

10. The process of claim 9 wherein the source of anions iii) is the carboxylic acid prepared in step a).

11. The process of claim 8 wherein the carboxylic acid as prepared in step a) is used as a reaction diluent in both step a) and step b).

12. The process of claim 9 wherein the phosphorus containing ligand of ii) is a bidentate diphosphine.

13. The process of claim 12 wherein the bidentate diphosphine ligand of ii) is 1,2-P,P'-di(2-phospha-1,3,5,7-tetramethyl-6,9,10-trioxatricyclo[3.3.1.1{3,7}decyl)-methylene]-benzene.

* * * * *